US006607508B2

(12) United States Patent
Knauer (10) Patent No.: US 6,607,508 B2
(45) Date of Patent: Aug. 19, 2003

(54) VIAL INJECTOR DEVICE

(75) Inventor: Peter M. Knauer, Sandy, UT (US)

(73) Assignee: Invivotech, Inc., Park City, UT (US)

( * ) Notice: Subject to any disclaimer, the term of this patent is extended or adjusted under 35 U.S.C. 154(b) by 0 days.

(21) Appl. No.: 09/844,735

(22) Filed: Apr. 27, 2001

(65) Prior Publication Data

US 2001/0037087 A1 Nov. 1, 2001

Related U.S. Application Data

(60) Provisional application No. 60/200,723, filed on Apr. 27, 2000.

(51) Int. Cl.[7] .......................... A61M 37/00; A61M 5/20
(52) U.S. Cl. ........................ 604/131; 604/134; 604/137
(58) Field of Search ................................ 604/131, 134, 604/137, 93.01, 140, 141, 148, 411, 412, 403, 414, 533, 538, 905

(56) References Cited

U.S. PATENT DOCUMENTS

| | | | | |
|---|---|---|---|---|
| 1,916,428 A | * | 7/1933 | Kovacs | 604/148 |
| 3,040,743 A | * | 6/1962 | Naess | 604/148 |
| 4,204,539 A | * | 5/1980 | Van Brugge | 604/148 |
| 4,759,755 A | | 7/1988 | Hein et al. | |
| D304,616 S | | 11/1989 | Dunlap et al. | |
| 5,026,349 A | | 6/1991 | Schmitz et al. | |
| 5,171,214 A | * | 12/1992 | Kolber et al. | 206/222 |
| D343,897 S | | 2/1994 | Rand et al. | |
| 5,429,256 A | | 7/1995 | Kestenbaum | |
| 5,514,097 A | | 5/1996 | Knauer | |
| 5,634,909 A | | 6/1997 | Schmitz | |
| 5,658,259 A | | 8/1997 | Pearson et al. | |
| 5,681,291 A | | 10/1997 | Galli | |
| 5,688,251 A | | 11/1997 | Chanoch | |
| 5,779,677 A | | 7/1998 | Frezza | |
| 5,782,815 A | | 7/1998 | Yanai et al. | |
| 5,807,346 A | | 9/1998 | Frezza | |
| 5,820,602 A | | 10/1998 | Kovelman et al. | |
| 5,897,526 A | | 4/1999 | Vaillancourt | |
| 6,003,566 A | | 12/1999 | Thibault et al. | |
| 6,090,082 A | | 7/2000 | King et al. | |
| 6,099,503 A | | 8/2000 | Stradella | |
| 6,149,626 A | * | 11/2000 | Bachynsky et al. | 604/134 |
| 6,174,304 B1 | | 1/2001 | Weston | |
| 6,189,580 B1 | | 2/2001 | Thibault et al. | |
| 6,203,530 B1 | | 3/2001 | Stewart, Sr. | |
| 6,209,738 B1 | | 4/2001 | Jansen et al. | |
| 6,210,369 B1 | | 4/2001 | Wilmot et al. | |
| 6,312,149 B1 | | 11/2001 | Sjovall et al. | |

* cited by examiner

Primary Examiner—Ehud Gartenberg
Assistant Examiner—John K Fristoe, Jr.
(74) Attorney, Agent, or Firm—Beyer Weaver & Thomas LLP (57) ABSTRACT

An automatic medicament delivery device and corresponding method for use with a standard needle assembly and a standard vial container that contains a medicament is disclosed. A user attaches the needle assembly and the vial container to the device. The user can transfer and measure a dose from the vial container into the device. When the user presses the tip of the device against the injection site, a needle of the needle assembly is automatically injected into the user and the measured dose is delivered into the user through the needle. When the user removes the device from the injection site, the device is re-cocked for the next injection.

14 Claims, 11 Drawing Sheets

VIAL INJECTOR DEVICE

This application claims the benefit of Provisional application No. 60/200,723 filed Apr. 27, 2000.

FIELD OF THE INVENTION

This invention relates to medicament delivery devices. More specifically, the invention relates to self-administered automatic medicament delivery devices.

BACKGROUND OF THE INVENTION

Self administered subcutaneous or intramuscular injections are well known in the medical arts and have long been considered standard treatment, such as diabetics, who require fixed or measured doses of medicament on a regular and relatively frequent basis. Further, newer treatments, such as growth hormone injections, also require self administered injections on a regular basis.

Self administered injections considerably decrease the cost of treatment and increase the quality of the patients life by decreasing or even eliminating the need for some visits to the doctor. Self administered injections also provide patients with the opportunity to privately administer their own treatment, without involving third parties, thus giving the patient a sense of independence and control.

Typically, self administered injections are rendered using pre-filled syringes or cartridges of pre-measured doses of medicament. However, such self administered injections suffer from several drawbacks and are particularly ill suited for use by children or patients with disabilities because they required the patient to manually insert an exposed needle in the tissue.

Drug manufacturers also spend significant cost and time producing pre-filled syringes or cartridges. A traditional vial, with a glass body and rubber stopper, is the least expensive and most readily available medicament container system.

Prior art pen injector apparatuses consist of four major components: (i) a pre-filled cartridge or syringe containing the medicament; (ii) a housing formed to receive the pre-filled cartridge or syringe; (iii) a mechanical dispensing assembly; and (iv) a double sided needle assembly that attaches to the receiving housing. Each of the four major components are described in detail below.

Prior art cartridges or syringes consist of a glass or plastic barrel with one open end and an opposite end with either a rubber seal or Luer Lock assembly to receive a needle. A rubber plunger is placed in the open end of the barrel to seal off the assembly slide forward to dispense liquid. Considerable amounts of lubrication, typically silicone, is applied to the plunger and barrel to reduce sliding friction.

Prior art housing assemblies are used to hold the cartridge or syringe in place during and after the injection process. Typically in barrel in shape, the housing has an opening on one end to facilitate receiving the cartridge or syringe. The opposite end has a smaller opening that allows one end of a double ended needle to penetrate a rubber septum in the cartridge, and mounting threads to receive the body of the needle assembly.

Prior art dispensing assemblies typically consist of a barrel shape that attaches to the housing assembly on one end, and a dose setting mechanism on the opposite end. The dose setting mechanism is typically an analog dial or electronic counting system that allows the patient or user to adjust the medicament dose.

Prior art needle assemblies consist of a double ended cannula, which on one end, penetrates the rubber septum of the cartridge seal and on the other end is used to penetrate the subcutaneous or intra muscular space of the human anatomy to deliver the dose. A threaded barrel typically is used to attach the needle assembly to the housing assembly.

Typically, prior art pen injection devices patients or caregivers to manually insert an exposed needle into his or her own tissue. This can be a traumatic experience, particularly for patients requiring frequent or daily injections.

Further, when a patient finishes his or her injection, current injection devices make no provisions for shielding the exposed needle from in advertent sticks. New regulations in certain states now require caregivers to be protected from exposed needles.

SUMMARY OF THE INVENTION

In summary, the invention is an automatic medicament delivery device and corresponding method for use with a needle assembly and a vial container that contains a medicament. The device comprises a disposable transfer system and an injector body. The disposable transfer system is configured to enable a user to attach the vial container to the disposable transfer system. The injector body is configured to enable the user to attach the disposable transfer system with the vial container attached thereto to the injector body and to attach the needle assembly to the disposable transfer system after the disposable transfer system is attached to the injector body. The disposable transfer system and the injector body are further configured to cooperatively enable the user to transfer and measure the dose from the vial container into the disposable transfer system after the disposable transfer system is attached to the injector body. The disposable transfer system and the injector body are even further configured to cooperatively enable the user to automatically inject a needle of the needle assembly into the user and deliver the measured dose from the disposable transfer system to the user through the needle. This is done after the needle assembly is attached to the disposable transfer system and when the injector body is pressed against an injection site of the user.

DETAILED DESCRIPTION

Figure 1:
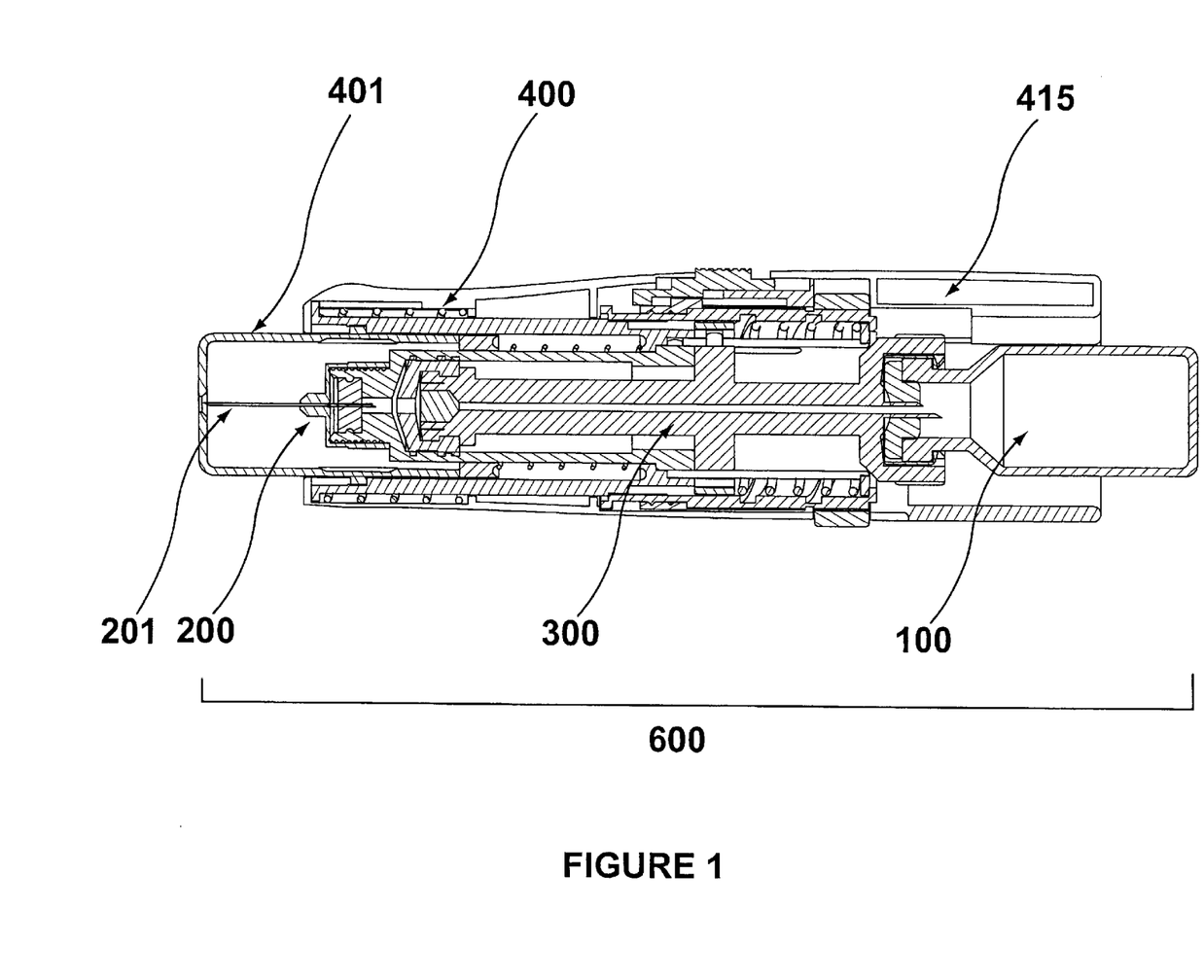
FIG. 1 is a cut view drawing of an automatic medicament delivery device in accordance with the present invention.
Figure 2:
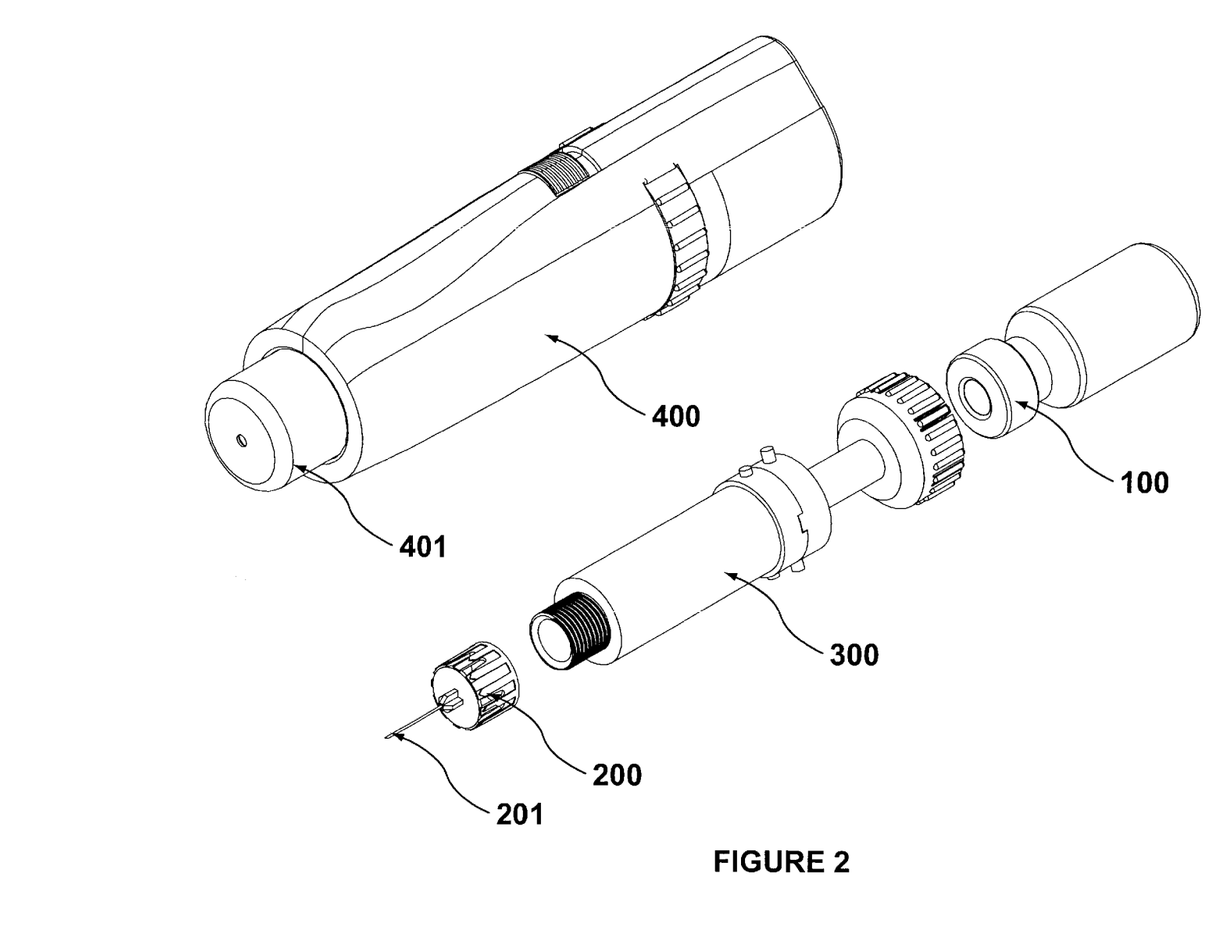
FIG. 2 is an isometric view drawing of the automatic medicament delivery device of FIG. 1.

Referring to FIGS. 1 and 2, there is shown an automatic medicament delivery device [600] according to one embodiment of the invention. The device comprises an injector body [400] and a disposable transfer system [300]. The device is used in conjunction with a standard glass vial container [100] containing a medicament and a disposable needle assembly [200].

To provide the proper context for describing the automatic medicament delivery device [600] in more detail later, a brief general description of the configuration and operation of the disposable transfer system [300] and the injector body [400] will be provided here. First, the standard glass vial container [100] is irreversibly attached to the disposable transfer system by snapping the standard glass vial container into place. The disposable transfer system, with the standard glass vial container attached, is inserted into and removably attached to the injector body [400] in preparation for injection. A measured (or set) dose of the medicament is transferred from the standard glass vial container into the disposable transfer system by selectively dialing the dose into the disposable transfer system. The disposable needle assembly [200] is removably attached to the front end of the disposable transfer system by removing the tip trigger piece [401] of the injector body and threading on the disposable needle assembly. The tip trigger piece is reattached and the user (e.g., patient or caregiver) initiates the injection by placing the tip trigger piece against the injection site and pressing downward. Insertion of the needle [201] of the disposable needle assembly [200] is automatically triggered as the tip trigger piece retracts into the injector body. Once the needle reaches its full penetration depth, the medicament is automatically delivered via the disposable transfer system, through the needle and into the subcutaneous or intra muscular layer of the skin. Upon completion of the medicament delivery, the user pulls the injector body away from the injection site and the tip trigger piece keeps the needle hidden as it returns to an extended position. This action also locks the tip trigger piece into place to prevent inadvertent needle sticks. The tip trigger piece can be unlocked only by removing the piece to replace a needle in preparation for another injection.

Figure 3:
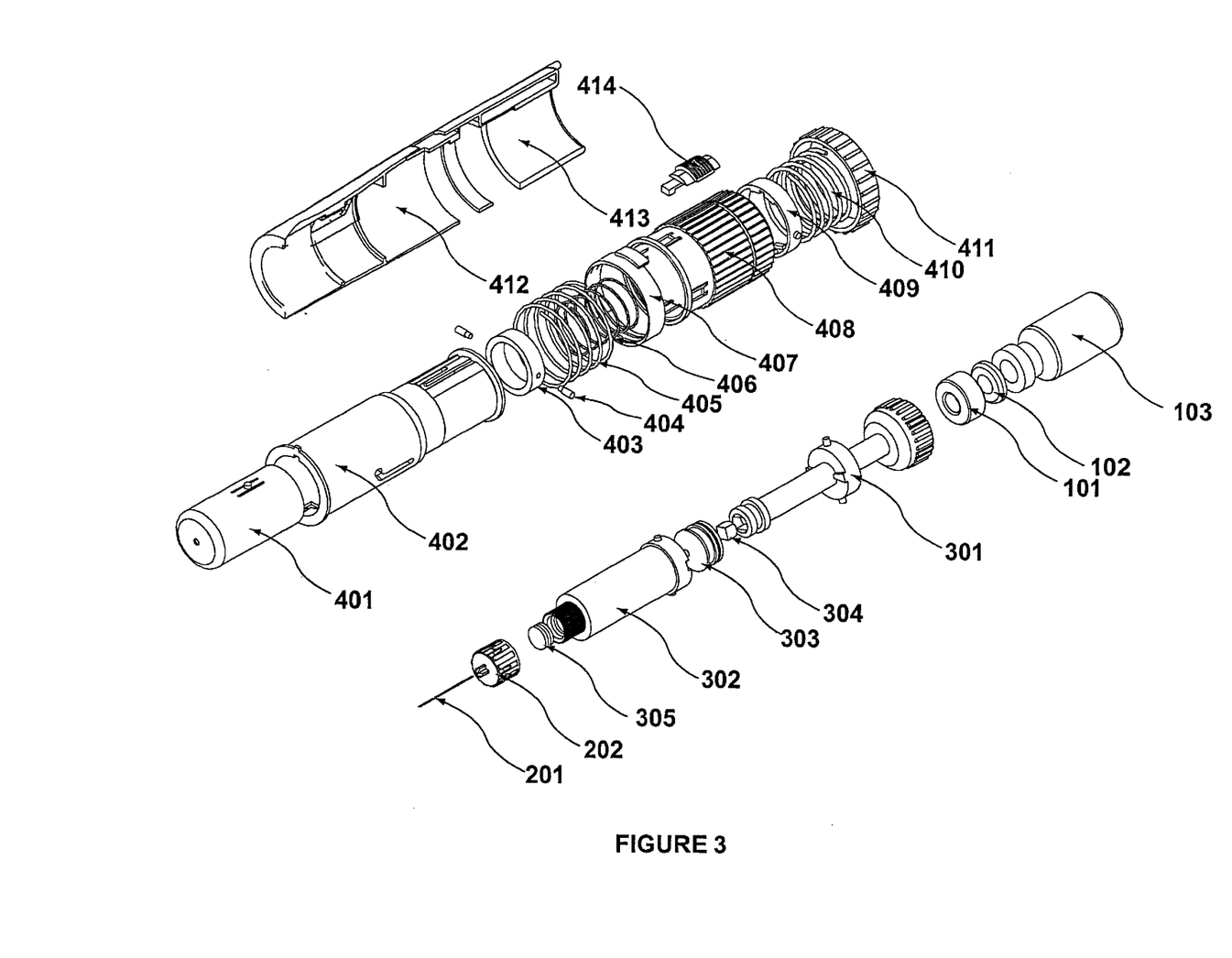
FIG. 3 is an isometric exploded view drawing of the automatic medicament delivery device of FIGS. 1 and 2.

FIG. 3 shows some of the component parts [301 to 305] of the disposable transfer system [300], some of the component parts [401 to 414] of the injector body [400], some of the component parts [201 and 202] of the needle assembly [200], and some of the component parts [101 to 103] of the glass vial container [100]. These component parts will be discussed in conjunction with the more detailed discussion of the configuration and operation of the disposable transfer system [300] and the injector body [400].

Figure 4:
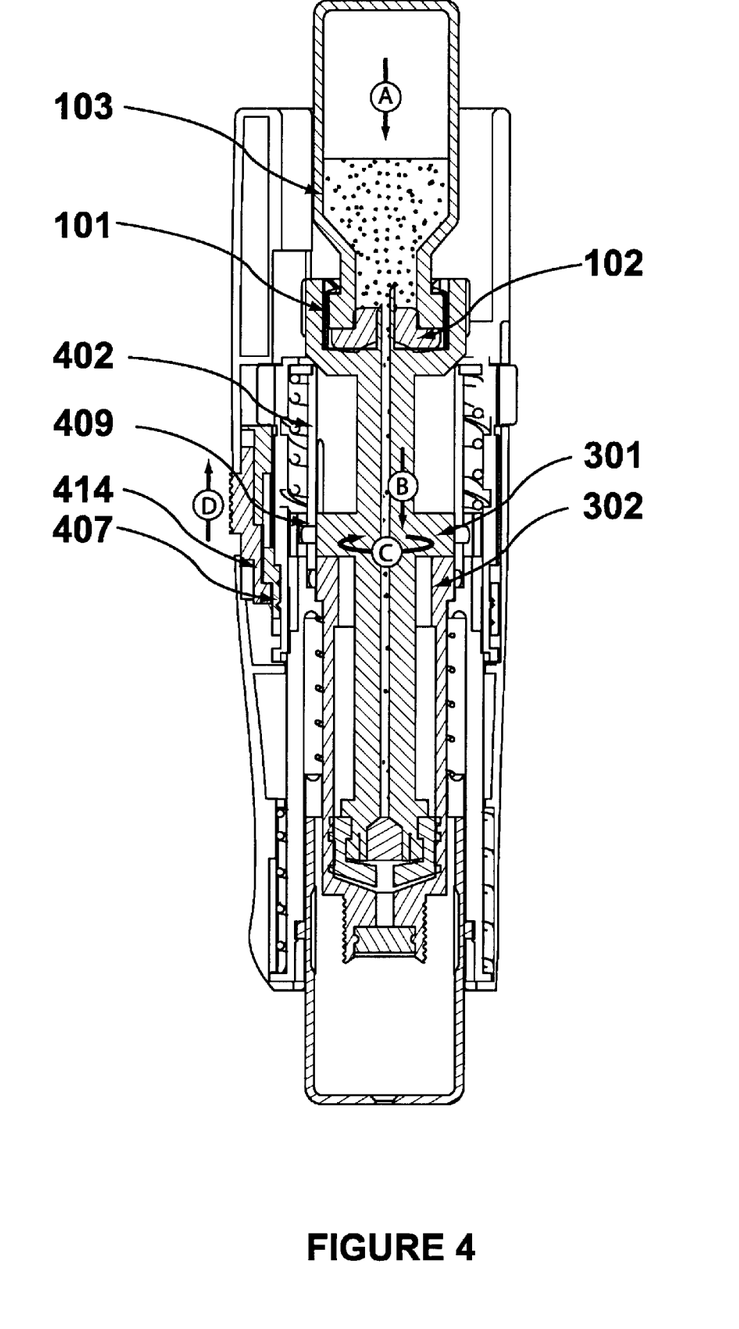
FIG. 4 is a cut view drawing highlighting attaching a standard glass vial container to the disposable transfer system of the automatic medicament delivery device of FIGS. 1 to 3.

FIG. 4 shows the details of attaching the disposable transfer system [300] to the injector body [400] so that the disposable transfer system and the injector body can work cooperatively in measuring (or setting) and delivering a dose of the medicament in the glass vial container [100]. The glass vial container is first snapped onto the plunger rod [301] (Step A). Clips on the plunger rod are designed to bend away from the cap [101] of the standard glass vial container. Once the cap passes by, the clips grip the neck of the glass vial [103], irreversibly locking and snapping it into place. A hollow spike on the plunger rod penetrates the rubber stopper [102] of the standard glass vial container as the standard glass vial container is snapped into place. This opens a pathway for the medicament to pass from the standard glass vial container, through the plunger rod [301] and rubber plunger [303], and into the syringe barrel [302], as shown in FIG. 5.

The disposable transfer system [300], with the standard glass vial container [100] attached, is then attached to the injector body [400] by aligning the pins on the plunger rod [301] and syringe barrel [302] with the corresponding slots in the dose ring [409] and on the main barrel [402] (Step B). The pins on the syringe barrel slide down the vertical portion of the slots on the main barrel until they reach the horizontal portions of the slots (i.e., a 90 degree turn) at the bottom of the slots. Rotating the disposable transfer system clockwise slides the pins into the horizontal portion of the slots and locks the plunger rod [301] and syringe barrel [302] into the main barrel and dose ring [409] (Step C). The injector body also needs to be reset at this point by depressing the reset button [414], which engages the ratchet ring [407], as explained below for FIG. 5 (Step D).

Figure 5:
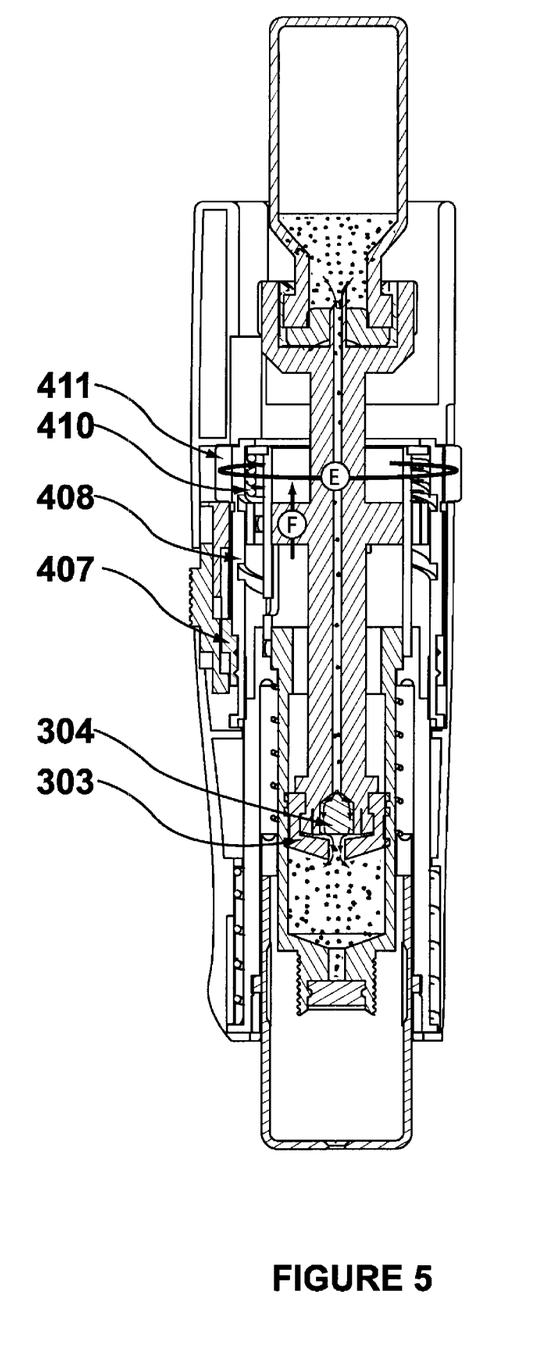
FIG. 5 is a cut view drawing highlighting measuring a dose of medicament and transferring the dose into the disposable transfer system of the automatic medicament delivery device of FIGS. 1 to 3.

FIG. 5 shows the details of measuring (or setting) and transferring a dose into the disposable transfer system [300] using the dose barrel [408], dose ring [409], dose spring [410], and dose dial [411] of the dial dose measuring (or setting) mechanism of the injector body [400]. Once the plunger rod [301] is locked into the dose ring [409], the user can measure (or set) a dose of medicament into the injector body by selectively turning the dose dial [411] in a clockwise direction (Step E) a desired amount. The dose dial is attached by slots to the dose barrel [408], which allows dependent rotation of the two parts, but independent translation. This design allows the dose ring to remain in the same position while the internal components of the injector body [400] translate during the injection process. Rotating the dose barrel engages the pins of the dose ring into the helical slots of the dose barrel, resulting in the translation of the dose ring and the plunger rod (Step F), which is attached to the plunger [303]. Discretely controlling the rotation of the dose barrel results in the precise translation of the plunger rod and plunger. The dose spring [410] compresses as the dose ring translates, providing the motive force to push the plunger rod downwards during injection. Ratchets on the outer surface of the dose barrel engage with the ratchet ring [407] to prevent the rotation of the dose barrel (and translation of the plunger rod) until an injection is triggered.

The translation of the plunger rod [301] and plunger [303] transfers the medicament from the vial into the syringe barrel [302] in preparation for an injection. As the plunger rod translates away from the front end of the injector body [400], a volume is created between the plunger [303] and the syringe barrel [302]. The seal between the plunger and syringe barrel ensures that the volume is created under a vacuum. The medicament in the vial, under ambient pressure, is pushed into the volume between the plunger and syringe barrel. A check valve [304] prevents the flow of medicament back into the vial when the direction of the plunger is reversed during an injection.

As shown in FIG. 1, an optional programmed electronic module [415] may interface with the dial dose measuring mechanism to generate electronic data representing the measured dose. The electronic module includes a display, such as an LCD (liquid crystal display), to display the measured dose from the electronic data. The electronic module is capable of tracking the measured dose history from injection to injection and is capable of downloading the electronic data representing the measured dose history to a remote personal computer or other device.

Figure 6:
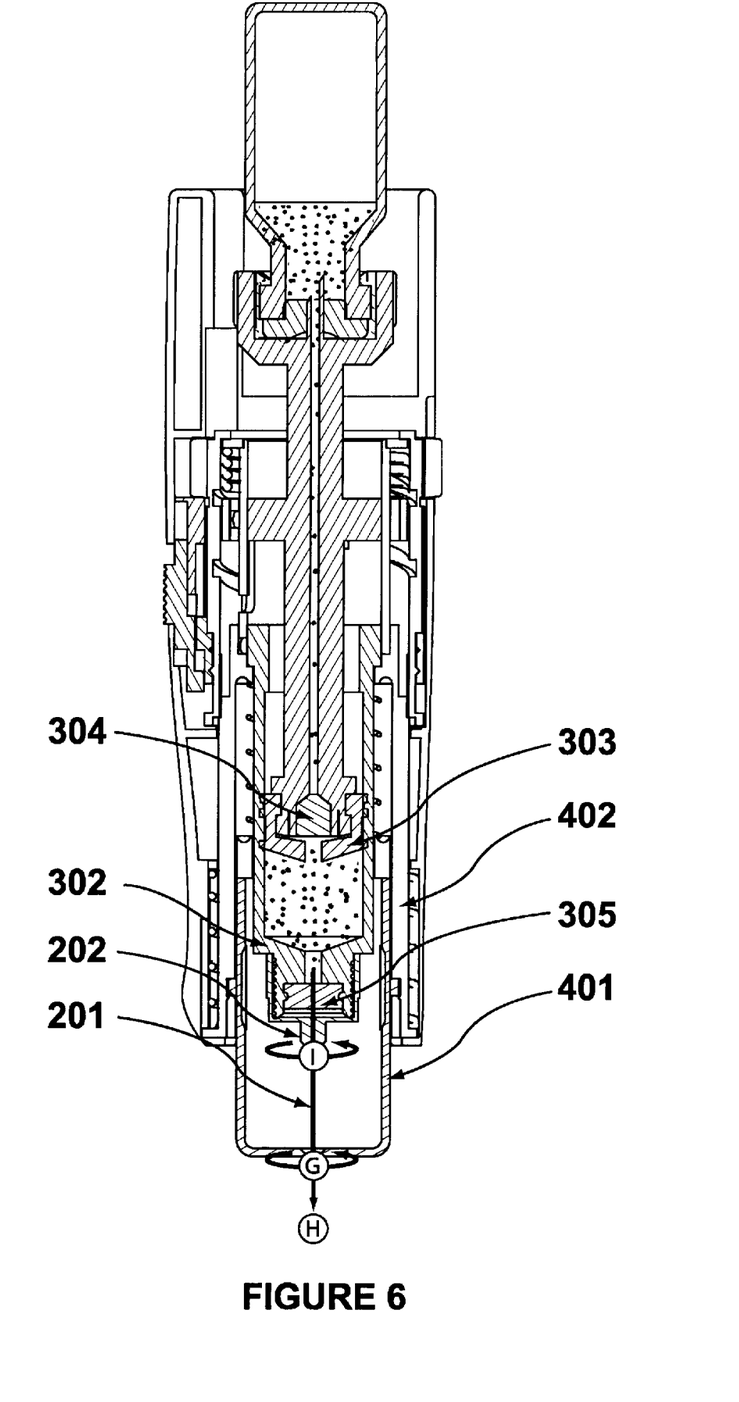
FIG. 6 is a cut view drawing highlighting attaching a disposable needle assembly to the disposable transfer system of the automatic medicament delivery device of FIGS. 1 to 3 and attaching the tip trigger piece of the injector body of the automatic medicament delivery device.

FIG. 6 shows the details of attaching the disposable needle assembly [200]. The needle assembly is of standard design, with threads on the interior surface of the needle hub [202]. The tip trigger piece [401] must be removed prior to attaching the needle assembly. The pins on the tip trigger disengage from the slots on the interior surface of the main barrel [402] by twisting the piece counter clockwise and pulling away from the injector body (Steps G,H). The interior threads of the needle hub match the threads on the syringe barrel [302]. The needle assembly is attached by threading clockwise onto the syringe barrel (Step I). The cannula [201] penetrates the rubber plug [305] in the syringe barrel as the needle is attached. The needle can not be attached prior to dose setting because the volume between the plunger and syringe barrel needs to be sealed in order to create a vacuum. Alternately, a check valve similar in design as [304] can be placed between the rubber plug and plunger, which would enable the attachment of the needle assembly at any time during the injector preparation process. Once the needle assembly has been attached, the tip trigger piece [401] is reattached and put into the unlocked position with a twist in the clockwise direction. Failure to twist the tip trigger piece leaves the injector body [400] in a locked position, preventing inadvertent needle stick injury.

Figure 7:
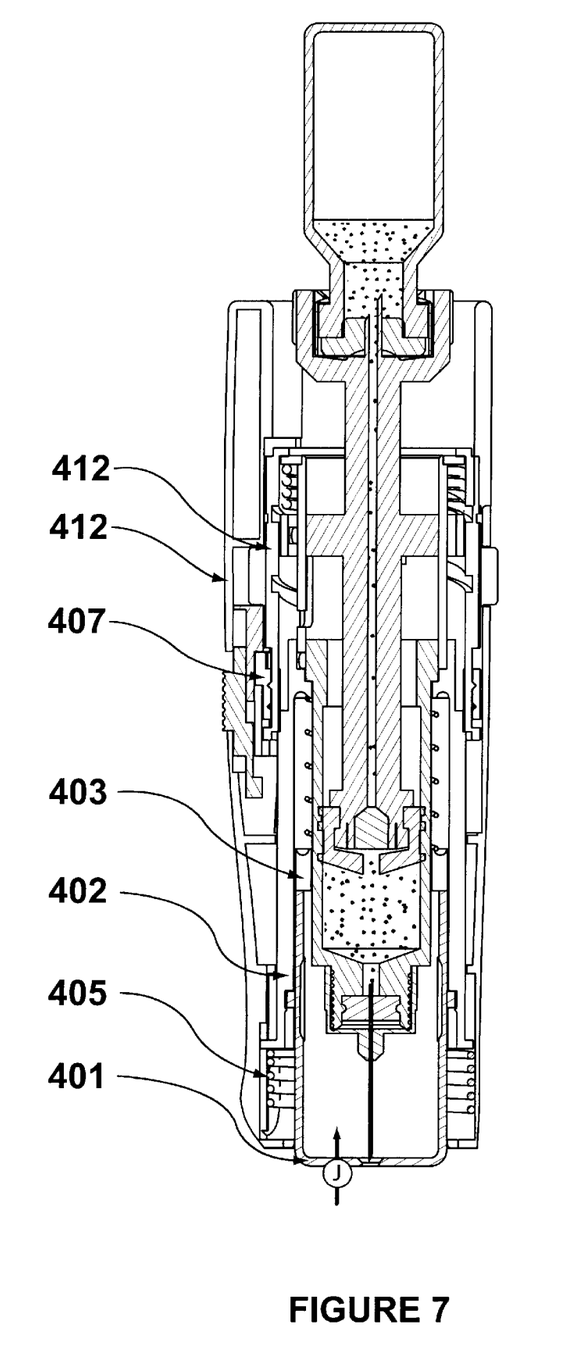
FIG. 7 is a cut view drawing highlighting the triggering of an injection performed by the automatic medicament delivery device of FIGS. 1 to 3.

FIG. 7 shows the details of initiating an injection sequence. A two step sequence is initiated by pressing the tip trigger piece [401] against the injection site (Step J). As the tip trigger piece retracts into the injector body [400], it pushes the main barrel [402], with all of the attached components (the needle assembly [200], disposable transfer system [300], dial dose measuring mechanism [408] to [411], and glass vial container [100]) upward. This motion also releases the ratchet ring [407] from the ratchets of the dose barrel [408]. The dose barrel is not however, free to rotate (and deliver the medicament) because the barrel is rotationally locked with the cosmetic shell [412] while in the retracted position. Once the barrel translates to a full forward position, it will be free to rotate.

Figure 8:
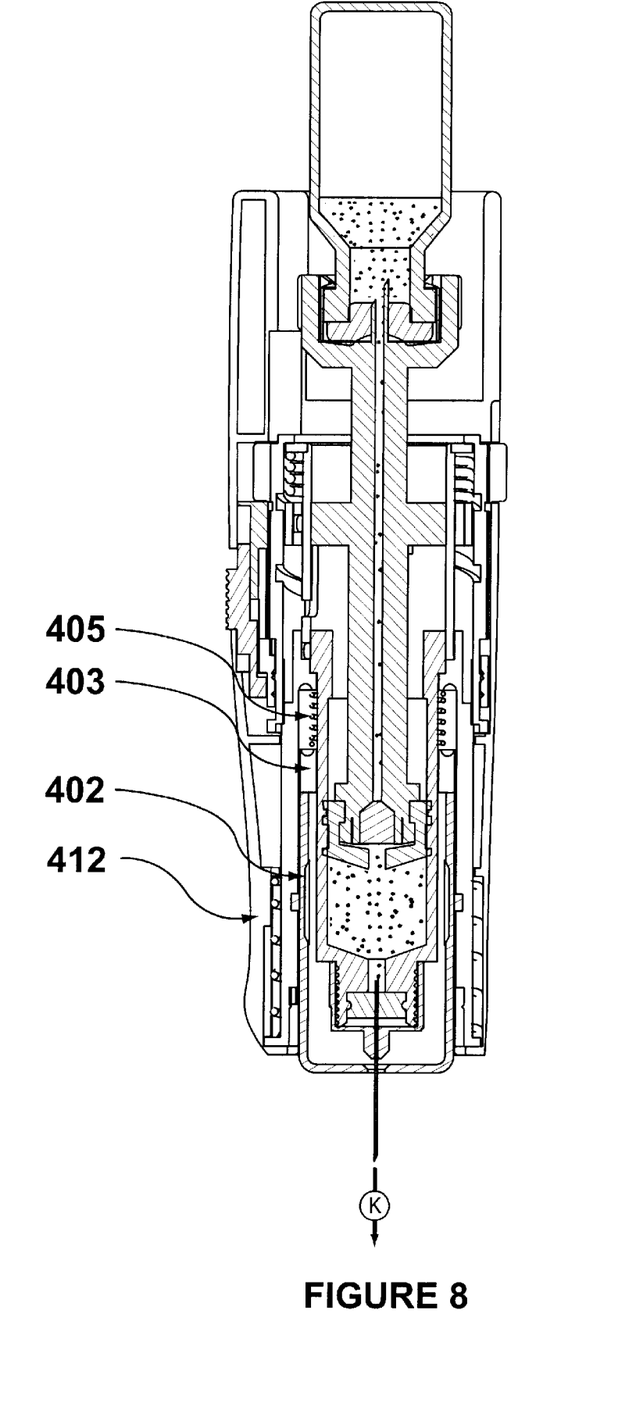
FIG. 8 is a cut view drawing highlighting the first step of the injection sequence performed by the automatic medicament delivery device of FIGS. 1 to 3.

FIG. 8 shows the details of the needle insertion sequence. At the maximum retracted position, the pins in the trigger ring [403], engage in the angled slots of cosmetic shell [412], rotating the ring clockwise. The pins, also locked into the main barrel [402], release the main barrel for translational movement (Step K). Once the main barrel has been released, the insertion spring [405] provides the motive force to translate the main barrel downward (with the needle assembly [200], disposable transfer system [300], dial dose measuring mechanism [408] to [411], and glass vial container [100]). The insertion spring provides enough force to insert the needle [201] into the injection site to a predetermined depth, either to the subcutaneous or intra muscular space.

Figure 9:
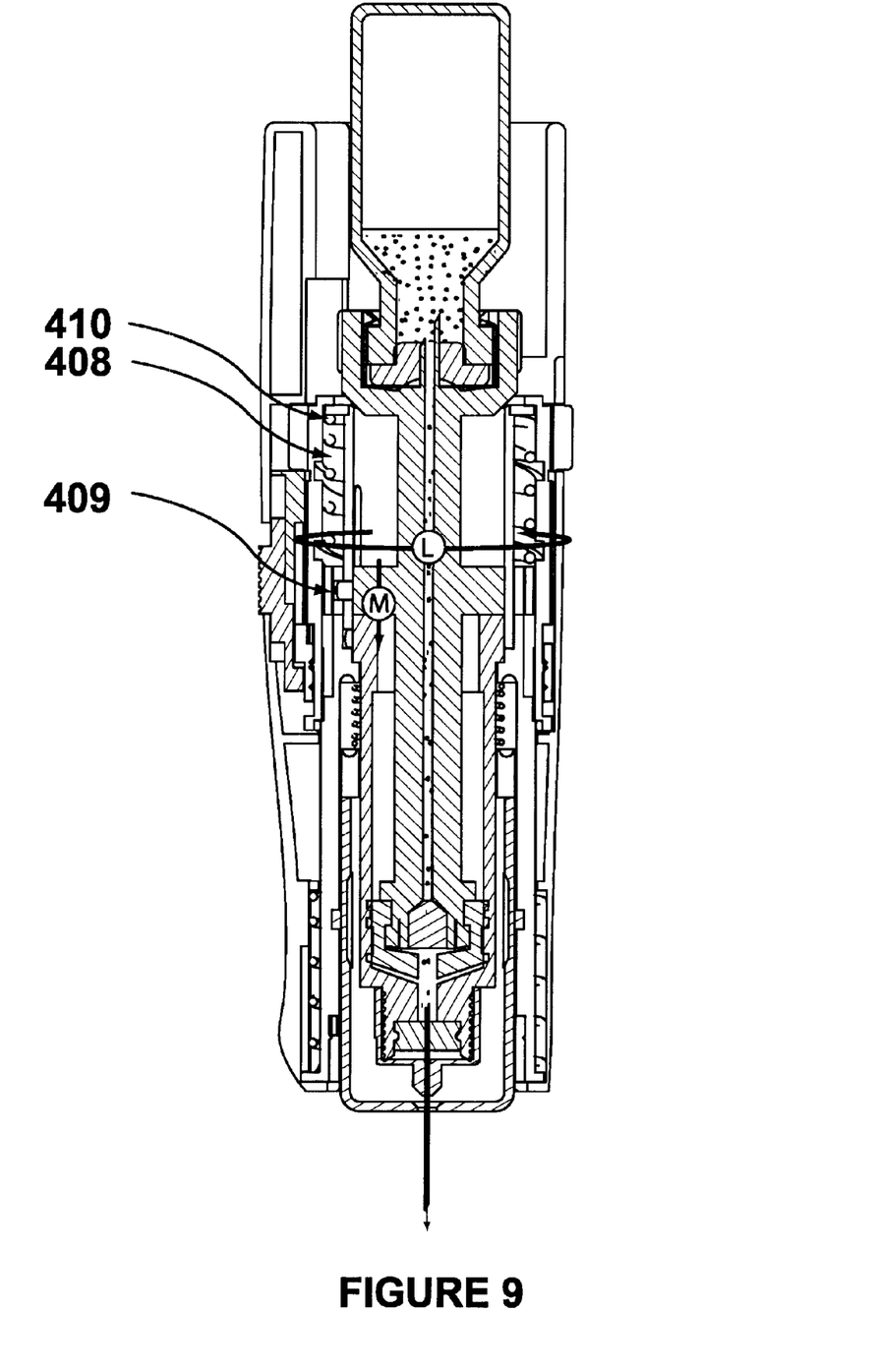
FIG. 9 is a cut view drawing highlighting the second step of the injection sequence performed by the automatic medicament delivery device of FIGS. 1 to 3.

FIG. 9 shows further details of the second step of the injection sequence. Once the needle [201] reaches its full penetration depth, the ratchets on the dose barrel [408] are released. This allows the dose barrel to rotate in a counter clock wise direction from the force of the dose spring [410] pressing against the dose ring [409] (the pins of the dose ring engage in the slots of the dose barrel). Once released, the dose barrel rotates all the way to completion (Step L), pushing the plunger rod [301] all of the way down (Step M), expelling all of the medicament that was transferred into the disposable transfer system during dose measuring (or setting).

Once the medicament is delivered, the user pulls the automatic medicament delivery device [600] away from the injection site. As the downward pressure is relieved, the tip trigger piece [401] begins to extend from it retracted position, keeping the needle assembly [200] hidden behind the tip trigger piece. The tip trigger piece locks into place after full extension due to the pins engaging in the slots of the main barrel [402], preventing inadvertent needle sticks after an injection. This same motion also cocks the dose spring [410] and the insertion spring [405], resetting the device for the next injection.

As those skilled in the art will appreciate, a user can use the automatic medicament delivery device [600] to repeatedly and accurately extract and measure doses of the medicament from the glass vial container [100] until it is empty. In doing so, the measured doses can be varied from dose to dose, as required by the user, or a fixed dose can be used every time.

Figure 10:
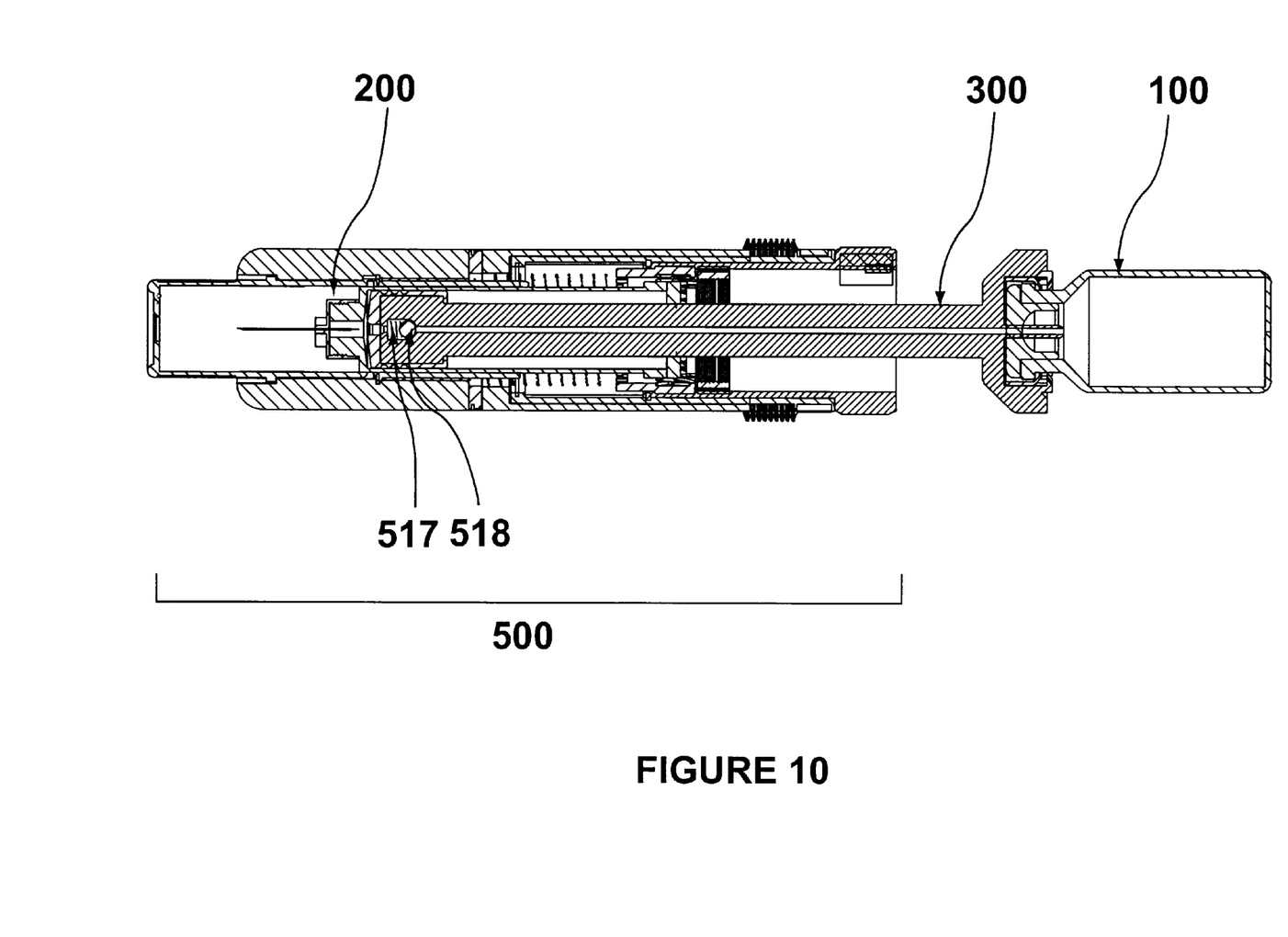
FIG. 10 is a cut view of an alternate embodiment of an automatic medicament delivery device.
Figure 11:
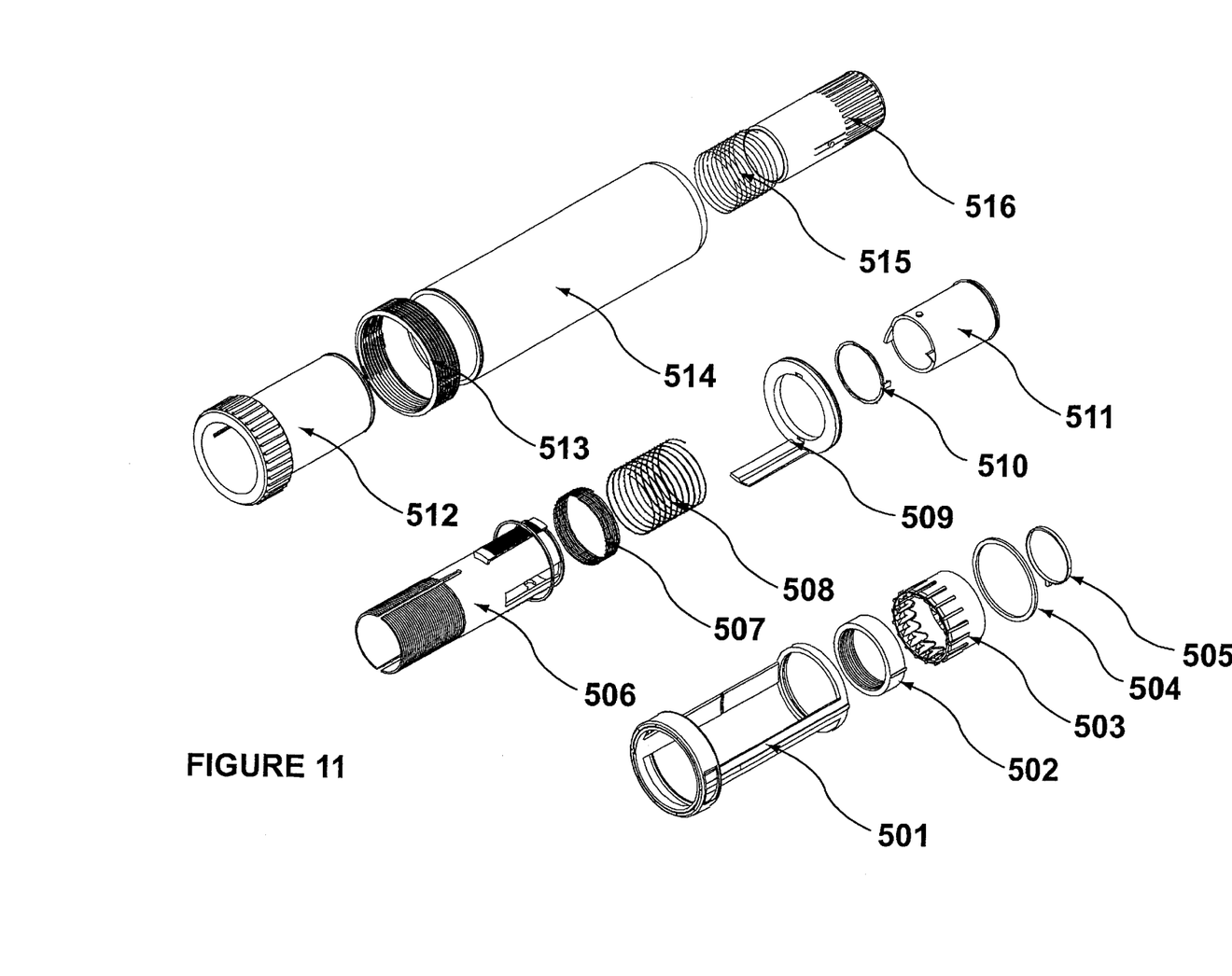
FIG. 11 is an isometric drawing view of the alternate embodiment of the automatic medicament delivery device of FIG. 10.

FIGS. 10 and 11 depict an alternative embodiment for an injector body [500]. The functionality is identical to the injector body [400] described above, but is differentiated by its parts [501 to 518].

In this alternative version of the injector body [500], a ball [517] and spring [518] are used as the check valve. The function of this check valve is identical to the check valve [304] described above. An alternative tip trigger piece [516] of the injector body [500] presses against a cylinder [511] that has angled ramps on its opposite end. The ramps engage with the clips on a ring [510] that force it to rotate counter clockwise. The rotation of the ring unlocks the translation of the main cylinder [506], which moves the parts [501] to [509] forward. The attached needle assembly [200] also moves forward, inserting the needle [201] into the subcutaneous or intra muscular space of the body. At the maximum forward motion of translation, the ramps on the main cylinder [506] engage with and rotate the release ring [509] clockwise, disengaging the ratchets on the main cylinder. This allows the dose ring [502] that is also locked into the plunger rod to translate forward, releasing medicament through the needle into the user.

A detailed description of the operation of one embodiment of the invention is provided above. While this description of the invention is made with reference to a specific embodiment, the description is only illustrative of the invention and is not to be construed as limiting the invention. Various modifications to the present invention can be made to the embodiment described above by those skilled in the art without departing from the true spirit and scope of the invention as defined by the appended claims.

What is claimed is:

1. An automatic medicament delivery device for use with a disposable needle assembly and a vial container that contains a medicament, the device comprising:

an injector body; and a disposable transfer system configured to enable a user to (a) attach the disposable needle assembly to the disposable transfer system and (b) attach the disposable transfer system to the injector body, the disposable transfer system including a syringe barrel, a plunger rod, and a plunger, the plunger rod and the plunger being connected to each other and translatable in the syringe barrel, the plunger rod being configured to enable the user to attach the vial container to the plunger rod; and the attached disposable transfer system and the injector body being further configured to cooperatively enable the user to (a) transfer and measure a dose of medicament from the attached vial container through the plunger rod and the plunger into the syringe barrel prior to delivery of the dose into the user and (b) when the injector body is pressed against an injection site of the user, automatically inject a needle of the attached disposable needle assembly into the user and deliver the dose from the syringe barrel into the user through the needle.

2. The automatic medicament delivery device of claim 1 wherein:

the injector body includes a dose measuring mechanism; and the dose measuring mechanism and the plunger and the plunger rod are configured to cooperatively enable the user to transfer and measure the dose from the vial container through the plunger rod and plunger and into the syringe barrel prior to delivery into the user.

3. The automatic medicament delivery system of claim 2 wherein the dose measuring mechanism is configured to enable the user to measure and transfer the dose by selectively controlling upward translation of the plunger rod and the plunger in the syringe barrel so as to create a vacuum in the syringe barrel which draws the medicament from the attached vial container through the plunger rod and plunger and into the syringe barrel.

4. The automatic medicament delivery system of claim 3 wherein:

the plunger rod includes pins;
the dose measuring system comprises:
  a dose dial; and
  a dose barrel attached to the dose barrel to allow dependent rotation with the dose dial and independent translation from the dose dial;
  a dose ring locked to the plunger rod when the disposable transfer system is attached to the injector body and rotatably engaged in the dose barrel for upward and downward translation of the plunger and plunger rod; and
  the dose ring, the dose dial, and the dose barrel being configured to cooperatively enable the user to selectively rotate the dose dial in a first direction so that the dose barrel and the dose ring dependently rotate and cause the selectively controlled upward translation of the plunger and the plunger rod.

5. The automatic medicament delivery system of claim 4 wherein the dose measuring system further comprises:

a dose spring in the dose barrel that presses against the dose ring and is compressed as a result of the selectively controlled translation of the plunger and the plunger rod; and
a ratchet ring;
the dose barrel including ratchets;
the ratchet ring and ratchets being configured to be cooperatively engaged until delivery of the dose to enable the user to selectively rotate the dose barrel in the first direction using the dose dial and prevent the dose barrel from rotating in a counter direction to the first direction due to the force of the compressed dose spring.

6. The automatic medicament delivery system of claim 5 wherein the injector body comprises:

a shell;
a tip trigger piece;
a trigger ring that presses against the tip trigger piece;
a main barrel configured to be lock to and unlocked from the trigger ring and to be locked to the syringe barrel when the disposable transfer system is attached to the injector body;
an insertion spring that presses against the main barrel and the shell;
the shell, the tip trigger piece, the trigger ring, and the main barrel being cooperatively configured to, when the tip trigger piece is pressed against an injection site by the user, enable (a) the trigger ring to translate upward and rotate so that the main barrel is unlocked from the trigger ring and released for downward translation, (b) compress the insertion spring so that the insertion spring provides the force to translate the main barrel downward when the main barrel is unlocked from the trigger ring so that the needle is injected into the user at the injection site, (c) release the ratchet ring from the ratchets when the main barrel is translated upward so that the dose barrel rotates in the counter direction due to the force of the compressed dose spring and translates the plunger and plunger rod downward to deliver the dose.

7. The automatic medicament delivery device of claim 2 wherein the disposable transfer system includes a check valve in the plunger that is configured to prevent the dose from flowing back into the vial container during delivery of the dose into the user.

8. An automatic medicament delivery device comprising:

an injector body; and
a disposable transfer system including a syring barrel, a plunger rod, and a plunger, the plunger rod and the plunger being connected to each other and translatable in the syringe barrel;
the disposable transfer system and the injector body being configured to cooperatively enable a user to (a) attach the disposable transfer system to the injector body, (b) transfer and measure a dose of medicament from a vial container attached to the plunger rod through the plunger rod and the plunger into the syringe barrel prior to delivery of the dose into the user, and (c) when the injector body is pressed against an injection site of the user, automatically inject a needle of a needle assembly attached to the disposable transfer system into the user and deliver the dose from the syringe barrel into the user through the needle.

9. The automatic medicament delivery device of claim 8 wherein:

the injector body includes a dose measuring mechanism; and the dose measuring mechanism and the plunger rod and the plunger are configured to cooperatively enable the user to transfer and measure the dose from the vial container through the plunger rod and plunger and into the syringe barrel prior to delivery into the user.

10. The automatic medicament delivery system of claim 9 wherein the dose measuring mechanism is configured to enable the user to measure and transfer the dose by selectively controlling upward translation of the plunger rod and the plunger in the syringe barrel so as to create a vacuum in the syringe barrel which draws the medicament from the attached vial container through the plunger rod and plunger and into the syringe barrel.

11. The automatic medicament delivery system of claim 10 wherein:

the plunger rod includes pins;

the dose measuring system comprises:
 a dose dial; and
  a dose barrel attached to the dose barrel to allow dependent rotation with the dose dial and independent translation from the dose dial;
  a dose ring locked to the plunger rod when the disposable transfer system is attached to the injector body and rotatably engaged in the dose barrel for upward and downward translation of the plunger and plunger rod; and
  the dose ring, the dose dial, and the dose barrel being configured to cooperatively enable the user to selectively rotate the dose dial in a first direction so that the dose barrel and the dose ring dependently rotate and cause the selectively controlled upward translation of the plunger and the plunger rod.

12. The automatic medicament delivery system of claim 11 wherein the dose measuring system further comprises:
 a dose spring in the dose barrel that presses against the dose ring and is compressed as a result of the selectively controlled translation of the plunger and the plunger rod; and
 a ratchet ring;
 the dose barrel including ratchets;
 the ratchet ring and ratchets being configured to be cooperatively engaged until delivery of the dose to enable the user to selectively rotate the dose barrel in the first direction using the dose dial and prevent the dose barrel from rotating in a counter direction to the first direction due to the force of the compressed dose spring.

13. The automatic medicament delivery system of claim 12 wherein the injector body comprises:
 a shell;
 a tip trigger piece;
 a trigger ring that presses against the tip trigger piece;
 a main barrel configured to be lock to and unlocked from the trigger ring and to be locked to the syringe barrel when the disposable transfer system is attached to the injector body;
 an insertion spring that presses against the main barrel and the shell;
 the shell, the tip trigger piece, the trigger ring, and the main barrel being cooperatively configured to, when the tip trigger piece is pressed against an injection site by the user, enable (a) the trigger ring to translate upward and rotate so that the main barrel is unlocked from the trigger ring and released for downward translation, (b) compress the insertion spring so that the insertion spring provides the force to translate the main barrel downward when the main barrel is unlocked from the trigger ring so that the needle is injected into the user at the injection site, (c) release the ratchet ring from the ratchets when the main barrel is translated upward so that the dose barrel rotates in the counter direction due to the force of the compressed dose spring and translates the plunger and plunger rod downward to deliver the dose.

14. The automatic medicament delivery device of claim 8 wherein the disposable transfer system includes a check valve in the plunger that is configured to prevent the dose from flowing back into the vial container during delivery of the dose into the user.

* * * * *